United States Patent [19]

Nelson

[11] 4,361,143
[45] Nov. 30, 1982

[54] SPLINT FOR HIND LEG OF AN ANIMAL

[76] Inventor: Richard M. Nelson, 23206 Marydale Dr., Elkhart, Ind. 46515

[21] Appl. No.: 255,900

[22] Filed: Apr. 20, 1981

[51] Int. Cl.³ .............................................. A61F 5/04
[52] U.S. Cl. .................................... 128/87 R; 119/96
[58] Field of Search ...................... 128/87 R, 89 R, 90, 128/165; 119/96, 127

[56] References Cited

U.S. PATENT DOCUMENTS

| | | | |
|---|---|---|---|
| 676,243 | 6/1901 | Rommel et al. | 119/127 |
| 1,624,861 | 4/1927 | Dewey | 119/127 |
| 3,416,519 | 12/1968 | Dowers | 128/87 R |
| 3,881,472 | 5/1975 | Lee | 128/89 R |
| 4,029,090 | 6/1977 | Dawson, Jr. | 128/87 R |

Primary Examiner—John D. Yasko
Attorney, Agent, or Firm—Oltsch, Knoblock & Hall

[57] ABSTRACT

A splint for a hind leg of an animal such as a dog or cat. The splint is shaped to conform to the normal shape of the hind leg of an animal and serves to sustain the weight of the animal while walking without imposing stress upon the leg in the region of the break.

4 Claims, 8 Drawing Figures

SPLINT FOR HIND LEG OF AN ANIMAL

SUMMARY OF THE INVENTION

This invention relates to a splint for a hind leg of an animal.

Heretofore, splints for the front legs of animals have been available but none have been offered for the hind legs of animals.

The splint of this application is shaped to conform to the normal shape of the hind leg of an animal. It fits one side of a leg and is securely fastened to the leg with a wrapping to prevent movement of the parts of the leg relative to each other. The splint has a portion at its lower end which fits around the animal's foot to prevent the animal's foot from touching the ground or from applying stress to the leg in the region of the break while the animal walks.

Accordingly, it is an object of this invention to provide a splint for a broken hind leg of an animal which will permit the animal to walk.

Another object of this invention is to provide a one-piece splint for a broken hind leg of an animal which conforms to the shape of the leg, protects the leg at the region of the break, and avoids imposition of stress at the region of the break while the animal walks.

Other objects of this invention will become apparent upon a reading of the following description.

BRIEF DESCRIPTION OF THE DRAWINGS

FIG. 6 is a rear view of the splint applied to a hind leg of an animal.

DESCRIPTION OF THE PREFERRED EMBODIMENT

The preferred embodiment illustrated is not intended to be exhaustive or to limit the invention to the precise form disclosed. It is chosen and described in order to explain the principles of the invention and its application and practical use to thereby enable others skilled in the art to utilize the invention.

Figure 7:
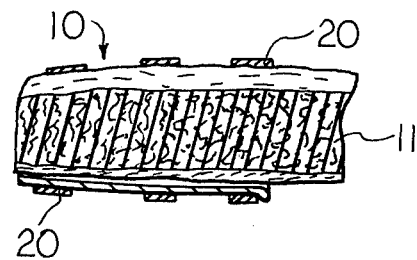
FIG. 7 is a section taken along line 7—7 of FIG. 4.
Figure 8:
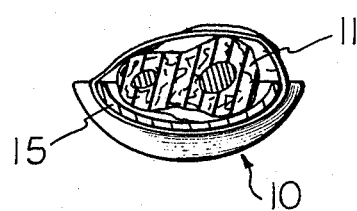
FIG. 8 is a section taken along line 8—8 of FIG. 4.

The splint 10 of this invention is illustrated in FIGS. 4–8 of the drawings. Splint 10 is shaped for application to a hind leg 11 of a dog 14, or other animal. Splint 10 is of one-piece construction and may be made of a molded material such as plaster with imbedded reinforcing fabric or plastic reinforced with a fabric or fiber filler. The splint is in the general shape of and of a size to receive the hind leg 11 of the animal 14 and is formed of rigid non-flexible material to prevent movement of the injured part of the leg. The splint 10 is curved or C-shaped in cross section as best seen in FIG. 8 and may be provided with an adhered fabric or cushioning liner 15. The lateral extent of the splint is adequate to receive approximately one half or one side of the leg as best seen in FIGS. 6 and 8.

Figure 1:
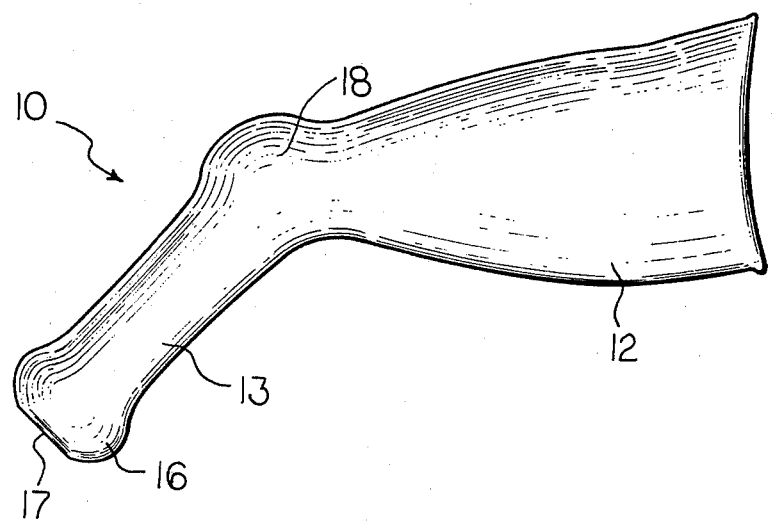
FIG. 1 is a plan view of a splint for the thigh and calf of a hind leg of an animal.
Figure 2:
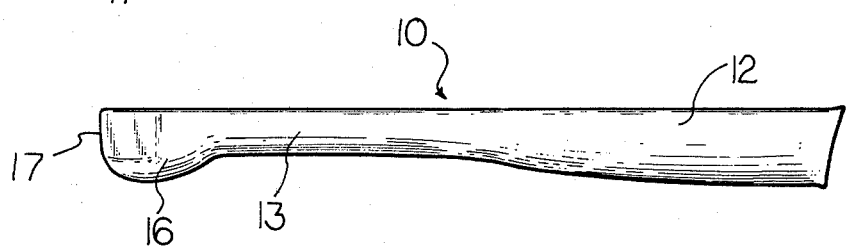
FIG. 2 is a side view of a splint for the thigh and calf of a hind leg of an animal.
Figure 3:
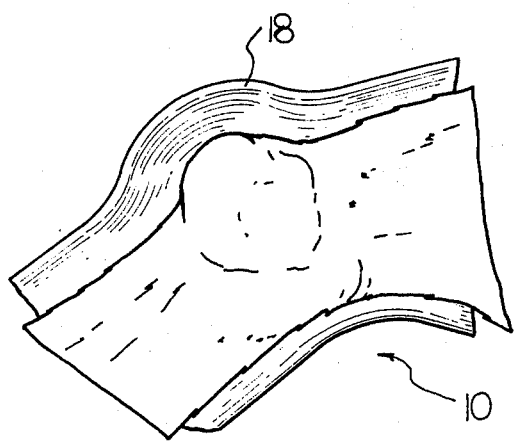
FIG. 3 is a fragmentary plan view of the stifle joint of a hind leg of an animal and of the portion of a splint receiving said joint.
Figure 4:
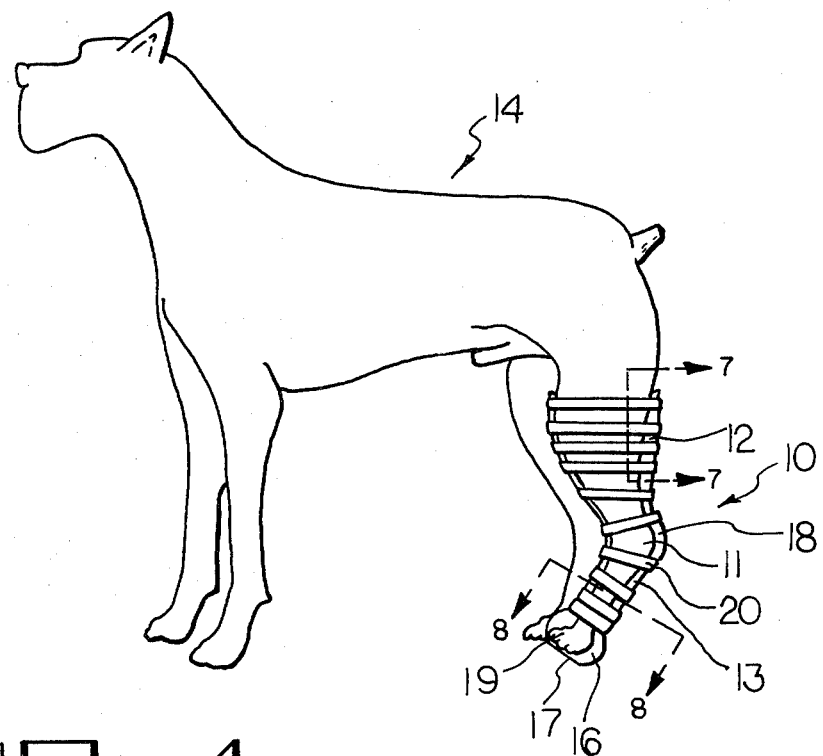
FIG. 4 is a side view showing the splint applied to a hind leg of an animal.
Figure 5:
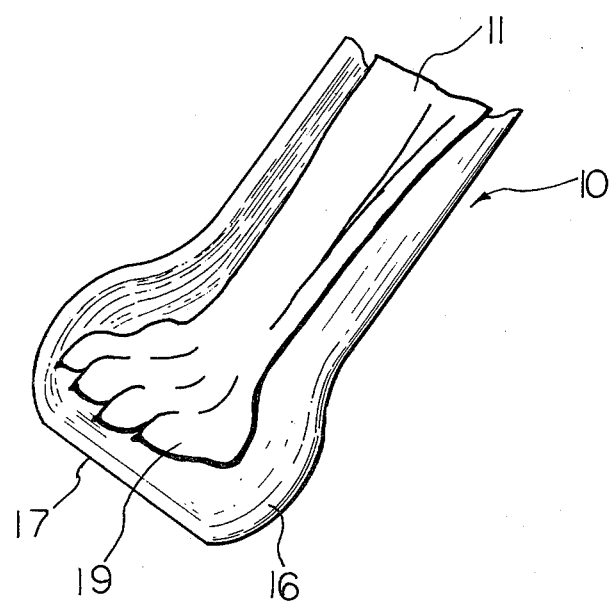
FIG. 5 is a fragmentary view of the portion of a splint receiving the lower portion of a hind leg of an animal.
Figure 2:
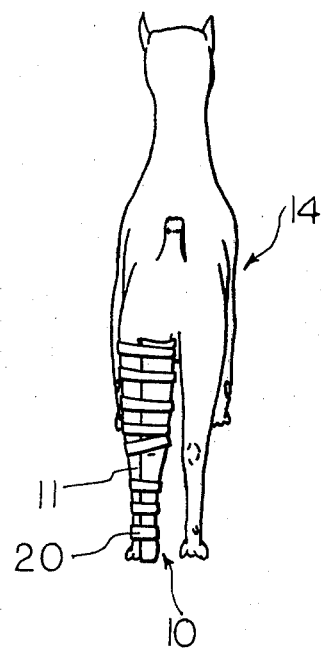

Splint 10 is sufficiently wide at its upper end 12 to accommodate the thick portion of the thigh of animal 14 and tapers toward its lower end 13 below the stifle joint to substantially conform to the shape of the leg. An enlargement 16 characterized by a transverse wall 17 is formed at the lower end of splint 10 to accommodate the animal's foot 19 with clearance. Intermediate its length the splint is enlarged at 18 to receive the stifle joint. The splint provides a depression or recess within its periphery within which leg 11 fits when the splint is applied to either the medial or lateral side of the leg. Splint 10 preferably does not entirely enclose leg 11 but receives enough of the leg to maintain it in normal position while a break is healing and to prevent discomfort. The splint is secured to the leg with tape 20 wound transversely around the splint and the exposed portion of the leg throughout the length of the splint and providing firm anchorage of the splint in the desired position on the leg, as seen in FIGS. 4, 6 and 7. The anchorage of the splint to the leg is sufficient to hold the splint firmly in position, with the foot or paw preferably spaced from end wall 17, as seen in FIG. 5.

This enables the animal to walk without applying longitudinal or lateral stress on the leg and on the portion of the leg at which it is broken.

It is to be understood that the invention is not to be limited to the details given above, but may be modified within the scope of the appended claims.

I claim:

1. A splint for a hind leg of an animal comprising an elongated rigid member having a shape substantially conforming to the shape of the medial or lateral side of an animal hind leg and having a bend intermediate its ends shaped to receive the stifle joint of the leg, said member being of substantially C-shape in cross section and of a size and interior shape to provide partial enclosure of said animal hind leg and extend at the posterior surface of the leg, said member being progressively enlarged upwardly and outwardly above said bend to receive the thigh of said hind leg, said member being tapered downwardly below said bend to receive the calf of said hind leg, said member being enlarged at its lower end to receive with clearance and project endwise beyond and below the foot or paw of said hind leg.

2. The splint of claim 1 wherein said splint is held to said hind leg with flexible tape encircling the splint and the leg substantially full length of the splint.

3. The splint of claim 2, wherein the enlarged lower end of said splint includes a transverse wall at its lower part spaced from the foot or paw of the animal.

4. The splint of claim 1, and a cushioning liner within said splint.

* * * * *